US006994270B2

United States Patent
Wongosari et al.

(10) Patent No.: US 6,994,270 B2
(45) Date of Patent: Feb. 7, 2006

(54) SEMI-ENCLOSED GEL DELIVERY DEVICE

(75) Inventors: Anita Wongosari, San Luis Obispo, CA (US); Michael C. Liptrot, Cambridge (GB); Padma Prabodh Varanasi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 11 days.

(21) Appl. No.: 10/712,507

(22) Filed: Nov. 13, 2003

(65) Prior Publication Data

US 2004/0129795 A1    Jul. 8, 2004

Related U.S. Application Data

(60) Provisional application No. 60/426,845, filed on Nov. 15, 2002.

(51) Int. Cl.
*A24F 25/00*     (2006.01)
*A61L 9/04*      (2006.01)
(52) U.S. Cl. ..................... 239/34; 239/41; 239/42; 239/47; 239/55; 239/58
(58) Field of Classification Search .............. 239/60, 239/55, 47, 35, 34
See application file for complete search history.

(56) References Cited

U.S. PATENT DOCUMENTS

| 2,733,956 | A | * | 2/1956 | Wenner | 239/57 |
| 3,239,145 | A | | 3/1966 | Russo | |
| 3,910,495 | A | * | 10/1975 | Cummings et al. | 239/58 |
| 4,157,787 | A | * | 6/1979 | Schwartz | 239/56 |
| 4,809,912 | A | * | 3/1989 | Santini | 239/60 |
| 5,060,858 | A | * | 10/1991 | Santini | 239/60 |
| 6,631,852 | B1 | * | 10/2003 | O'Leary | 239/60 |

FOREIGN PATENT DOCUMENTS

| GB | 778600 | 7/1957 |
| GB | 1359447 | 7/1974 |
| WO | WO 00/24434 | 5/2000 |

* cited by examiner

*Primary Examiner*—David A. Sherbel
*Assistant Examiner*—James S. Hogan

(57) ABSTRACT

A dispenser of actives having a linear release rate may be achieved by providing a volatile containing gel system wherein the gel system is proportioned in specified dimensional ratios, so that the sum of the rate of volatile release from directly exposed areas of the surface of the gel system and the rate of volatile release from areas of the surface of the gel system which are not in direct exposure to the atmosphere remains essentially constant through out the life of the dispensing device.

4 Claims, 1 Drawing Sheet

SEMI-ENCLOSED GEL DELIVERY DEVICE

RELATED APPLICATION

This application claims the benefit of U.S. Provisional Application Ser. No. 60/426,845, filed Nov. 15, 2002.

BACKGROUND OF THE INVENTION

The present invention relates to dispensers of volatile materials, which comprise a gel-type solid or semi-solid mass of material which is designed to release the maximum amount of volatile material over time, with a near-linear release rate. That is, the rate of release of volatile material is essentially uniform over the life of the dispenser.

The public is familiar with a number of solid or gel type air fresheners or dispensers of volatile materials. Most familiar are those which are sold to the public as Glade® air fresheners, produced by S. C. Johnson & Son, Inc., Racine, Wis., and Renuzit® air fresheners, a product of Dial Corporation, of Scottsdale, Ariz. While other dispensers of volatile materials, and air fresheners, are known, such as liquids incorporating wicks to assist in the evaporation of the liquid, and materials which may be heated to volatilize fragrances or other vaporizable components, the present invention is specifically directed to dispensers of volatile materials wherein a fragrance or other volatile active is encompassed within a solid or semi-solid material and is released over time by vaporization, to provide a pleasing fragrance, to release a pesticide or insect control material, to counter offensive odors, or to serve some other purpose. Aside from the problem of evaporation of volatile material from the dispenser prior to sale to the consumer, a problem associated with such dispensers is the drying, or shriveling, of the gel as the active material is released, resulting in an unattractive mass of hardened and emptied material to be disposed of, while the active, or volatile material is dispensed from the gel at an uneven or variable rate. That is, the fragrance or other active material is dispensed from the gel at a high rate upon initial exposure to the atmosphere, and more slowly as time passes, so that near the end of the life span of the dispensing device and its contained material, the volatile material is being released at rate which is much lower than the initial rate of release.

BRIEF SUMMARY OF THE INVENTION

We have found that a near-linear release of actives from a gel type dispenser of active materials may be achieved by providing the gel in a specific configuration, whereby delivery of the active to the atmosphere is enhanced.

Such systems may be classified, generally, as either a semi-enclosed gel, or an open gel system. For understanding, we have defined a semi-enclosed gel system as being one in which only part of the gel surface is exposed directly to flowing ambient air, and an open gel system as being one in which essentially the total available gel surface is exposed to the ambient air. The present invention addresses semi-enclosed gel systems.

The total release rate from an open gel ($TRR_{OG}$) is proportional to the surface area of the entire gel, as given by the following expression:

$$TRR_{OG} = K * C_o * A_D \quad (1)$$

Where $C_o$=Concentration of the active at the gel surface;
K=Mass Transfer Coefficient; and
$A_D$=Surface Area of the gel in a the completely open device.

Based on Equation 1, a close to zero-order release (i.e., constant release rate with time) can be obtained in a completely open gel system only if the surface area of the gel $A_D$ remains constant or is permitted to change only by a small fraction during the entire life of the product. Thus, by careful control of the configuration of the gel surface one is able to achieve a zero-order release of active materials from the gel system, providing a relatively constant release rate of the active material from initial opening until final disposal upon completion of evaporation of the active material.

However, in the case of a semi-enclosed gel (as opposed to an open gel), parameters in addition to surface area of the gel will influence the total release rate from the device. This observation is based on analysis of semi-enclosed gels. Based on our analysis, the total release rate from a semi-enclosed gel ($TRR_{SEG}$) is given by the formula:

$$TRR_{SEG} = K * C_o * A_D + \frac{C_o * \sqrt{K * \frac{A_D}{G} * D * A_P}}{\tanh\left(\sqrt{K * \frac{A_D}{G * D * A_P}} * H\right)}$$

Where,
  $A_D$=Surface Area of gel that is directly exposed to ambient flowing air;
  $A_P$=Area available for permeation of vapors generated within the enclosure;
  G=Gap Height;
  H=Gel Height;
  D=Diffusion Coefficient.

A careful examination of Equation 2 suggests that two parameters, namely, $A_D$ and $A_P$, play an important role in determining the total release rate from a semi-enclosed gel. The first term on the right hand side of equation 2 depicts the direct evaporative contribution from the exposed part of the gel to the total release rate. The second term denotes the permeation contribution of the vapors generated within the enclosure to the total release rate. Usually, the direct evaporative contribution decreases with time due to a decrease in the value of $A_D$ with time. However, the permeation contribution increases with time due to an increase in the value of $A_P$ with time (in fact, in some cases where the aspect ratio of the cross-section of the gel is close to 1, $A_P$ can go through a maximum). These counteracting effects of the first and second terms of equation 2 can lead to a close to a zero-order release rate, if applied as set forth hereinafter.

DETAILED DESCRIPTION OF THE INVENTION

Figure 1:
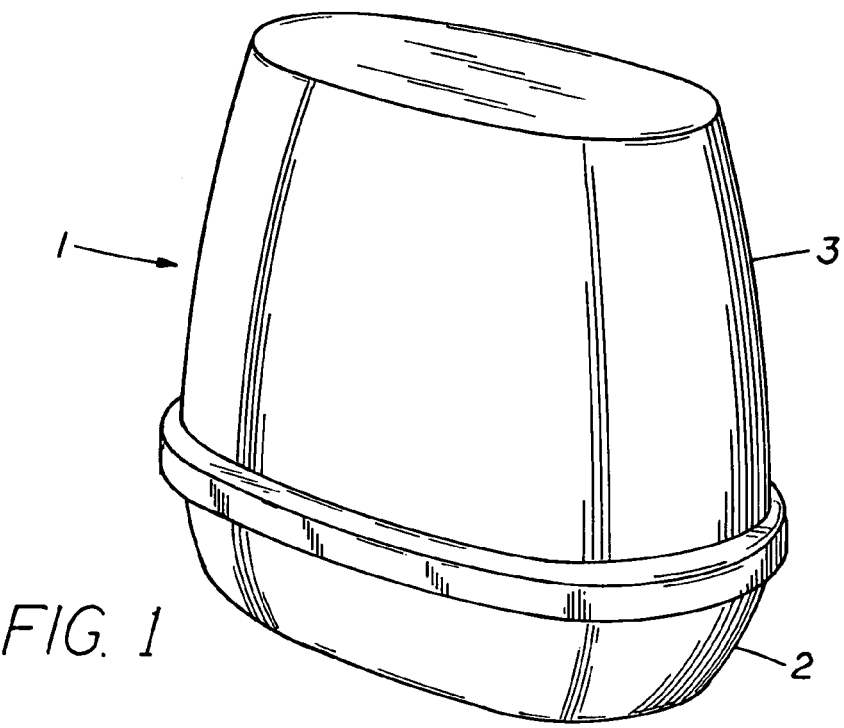
FIG. 1 illustrates the exterior container of a gel type dispenser of volatile materials in accordance with the present invention, in perspective view.

The present invention is related to gel type dispensers of active, or volatile materials, of the type commonly employed for air freshening, insect control, odor abatement, and the like. As shown in FIG. 1, such a dispenser (1), commonly comprises a base (2), and a cover or closure member (3) in which the base contains a volatile material, for example an air freshening deodorizer or fragrance, and in which the closure or cover is manually displaceable with respect to the base to provide means for control of the effective rate of volatilization or evaporation of the active material. Such cover or closure member commonly may be positively locked with respect to the base, as shown in FIG. 1, to prevent unintended evaporation or volatilization of the active material. After opening of the closure member to expose the contained gel, the cover may be adjusted relative to the base to permit substantial control or variation of the rate of volatilization of the gel. Said base and cover may preferably be of a molded plastic material, although other materials may be utilized. The container may further comprise support members or posts, around which the gel member is molded or formed, which members or posts, which may be singular or plural, provide support and strength to the gel material in the container. The gel materials to which the present invention applies are well known to practitioners of the art, as are the methods of manufacture and positioning in a container such as shown in FIG. 1, and need not be discussed in greater detail for the purpose of this invention. The provision of active or volatile materials, and the choice thereof for the purposes of the dispensing devices of this invention, are also well known, and as such need not be discussed further. Rather, the present invention is directed to the relationship of the dimensions of the gel or solid actives containing material of the device.

Figure 2:
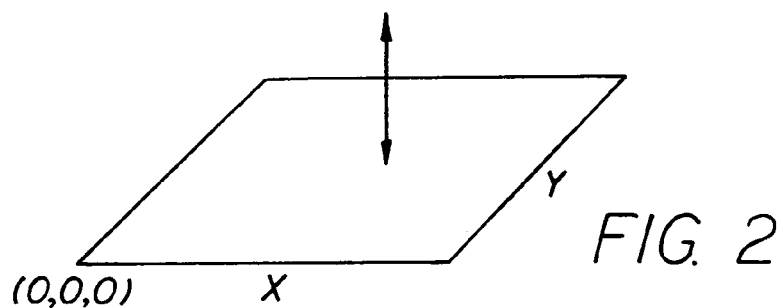
FIG. 2 illustrates the planar relationship of the coordinates of a gel system in accordance with the present invention.

To achieve a constant (zero-order) release rate for the volatile within a gel system, it is useful to consider the three dimensional configuration of the actives containing material (hereinafter the gel system), as shown in FIG. 2. In FIG. 2, dimensions x, y, and z are illustrated, having an origin point (0,0,0) at the intersection of said dimensions, wherein the gel system should be placed in such a way that it completely lies in the first quadrant of the x, y, z coordinate system and one point touches the origin point (0,0,0). The dimensions x, y, z and other parameters are defined thusly:

$x_I$=the longest dimension measured in the x direction of the projection of the directly exposed region of the gel system in the x-z plane at the initiation of volatilization;

$y_I$=the longest dimension measured in the y direction of the projection of the directly exposed region of the gel system in the x-y plane at the initiation of volatilization;

$z_I$=the longest dimension measured in the z direction of the projection of the directly exposed region of the gel system in the x-z plane at the initiation of volatilization;

$H_I$=the longest dimension measured in the z direction of the projection of the entire gel system in the x-z plane at the initiation of volatilization;

$x_F$=the longest dimension measured in the x direction of the projection of the directly exposed region of the gel system in the x-z plane at the end of volatilization;

$y_F$=the longest dimension measured in the y direction of the projection of the directly exposed region of the gel system in the x-y plane at the end of volatilization;

$z_F$=the longest dimension measured in the z direction of the projection of the directly exposed region of the gel system in the x-z plane at the end of volatilization; and $H_F$=the longest dimension measured in the z direction of the projection of the entire gel system in the x-z plane at the end of volatilization.

Figure 3:
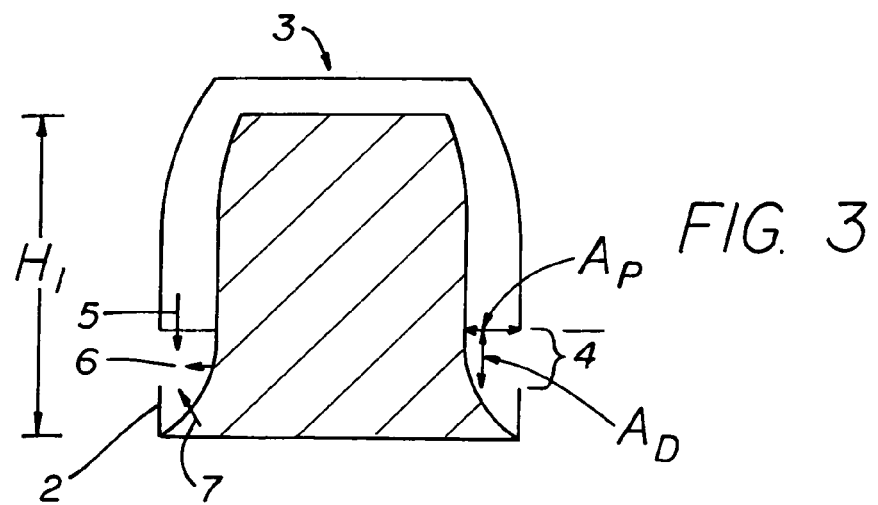
FIG. 3 illustrates the relationship between the container and the gel system of the present invention, showing the areas of release of the volatile material, i.e. the flux lines of the volatile material released.

As illustrated in FIG. 3, evaporation or flux of the volatile material may take place, in the direction of arrow 5, from the surface area not directly exposed to the atmosphere by movement of the cover 3 away from base 2, through gap 4, in the area defined as $A_P$, the Permeation Area, i.e., the area that is not directly exposed to the atmosphere, but is able to volatilize active material. Of course, evaporation or flux of volatile material also occurs through the gap, 4, in the direction of arrows 6 and 7, from the surface area which is directly exposed to the atmosphere, $A_D$.

To maintain a release rate that does not deviate significantly from zero-order release, the following ratios must be achieved:

$$x_I/y_I > 1.5, \text{ preferably } > 2.0, \text{ and most preferably } > 5.0; \quad (1)$$

$$H_I/z_I > 2.0, \text{ preferably } > 4.0, \text{ and most preferably } > 5.0; \quad (2)$$

$$x_F/y_F > 2.0, \text{ preferably } > 5.0, \text{ and most preferably } > 5.0; \quad (3)$$

4) $\dfrac{(A_D) \text{ final}/(A_D) \text{ initial}}{(A_P) \text{ final}/(A_P) \text{ initial}} > 0.19,$ preferably $> 0.4$, most preferably $> 0.7$ wherein: $A_D$=Surface Area of the gel that is directly exposed to ambient flowing air $A_P$=Area available for permeation of vapors generated within the enclosure 5) $\dfrac{(A_D) \text{ final}}{(A_D) \text{ initial}} > 0.65, \text{ preferably } > 0.75,$ and most preferably $> 0.9$, and, 6) $\dfrac{(AP) \text{ final}}{(AP) \text{ initial}} < 4.0, \text{ preferably } < 3.5,$ and most preferably $> 1.5$.

The preferred way to achieve a close to zero-order release rate is by ensuring that the percentage changes in both $A_D$ and $A_p$ during the life of the product are confined to certain limits. The following table shows the percentage changes associated with the parameters $A_D$ and $A_p$ during the life of the product in the case of the present invention and a conventional Renuzit® air freshener.

|  | Direct Evaporation Area ($A_D$) | | | Permeation Area ($A_P$) | | | |
| --- | --- | --- | --- | --- | --- | --- | --- |
|  | Initial | Final | Final/Initial | Initial | Final | Final/Initial | Aspect Ratio |
| Invention | 32.39 | 23.75 | 0.7333 | 6.88 | 26.6 | 3.866 | 1.75 |
| Renuzit | 26 | 9 | 0.3462 | 4.62 | 31.84 | 6.892 | 1 |

Based on the above table, we believe that by adhering to the following conditions, release rates that do not depart significantly from zero-order can be achieved:

the ratio of final to initial values of $A_D$ should be greater than 0.65;

the ratio of final to initial value $A_p$ should be less than 4.0; and the aspect ratio of the cross-section of the gel should be greater than 1.5.

Additional experiments demonstrated that by eliminating the permeation flux by covering the surface of that part of the gel that lies within the enclosure, it is feasible to have a zero-order release behavior for an extended period of the life of the product. This happens because the gel that lies within the enclosed region of the device serves as a reservoir to supply gel to the direct evaporation region so as to maintain the fractional change in its surface area to smaller values (a condition required for zero-order behavior according to equation 1).

What is claimed is:

1. A semi-enclosed gel system for release of volatile materials, wherein the dimensions of the gel system, in the x, y, and z dimensions, are such that:

a. $x_i/y_i > 1.5$, b. $H_i/z_i > 2.0$, c. $x_F/y_F > 2.0$, d. $\dfrac{(A_D)\text{ final}/(A_D)\text{ initial}}{(A_P)\text{ final}/(A_P)\text{ initial}} > 0.19$, wherein: $A_D$=Surface Area of the gel that is directly exposed to ambient flowing air $A_P$=Area available for permeation of vapors generated within the enclosure e. $\dfrac{(A_D)\text{ final}}{(A_D)\text{ initial}} > 0.65$, and f. $\dfrac{(AP)\text{ final}}{(AP)\text{ initial}} < 4.0$, wherein: $x_i$=the longest dimension measured in the x direction of the projection of the directly exposed region of the gel system in the x-z plane at the initiation of volatilization;

$y_i$=the longest dimension measured in the y direction of the projection of the directly exposed region of the gel system in the x-y plane at the initiation of volatilization;

$z_i$=the longest dimension measured in the z direction of the projection of the directly exposed region of the gel system in the x-z plane at the initiation of volatilization;

$H_i$=the longest dimension measured in the z direction of the projection of the entire gel system in the x-z plane at the initiation of volatilization;

$x_F$=the longest dimension measured in the x direction of the projection of the directly exposed region of the gel system in the x-z plane at the end of volatilization;

$y_F$=the longest dimension measured in the y direction of the projection of the directly exposed region of the gel system in the x-y plane at the end of volatilization;

$z_F$=the longest dimension measured in the z direction of the projection of the directly exposed region of the gel system in the x-z plane at the end of volatilization; and $H_F$=the longest dimension measured in the z direction of the projection of the entire gel system in the x-z plane at the end of volatilization.

2. The semi-enclosed gel system of claim 1, wherein:

a. the ratio of final to initial values of $A_D$ is greater than 0.65;

b. the ratio of final to initial value $A_p$ is less than 4.0; and c. the aspect ratio of the cross-section of the gel is greater than 1.5.

3. The semi-enclosed gel system of claim 2, wherein said volatile material is selected from the group consisting of materials employed for air freshening, insect control, and odor abatement.

4. The semi-enclosed gel system of claim 2, wherein said volatile material is a fragrance.

* * * * *